United States Patent
Wooh

(10) Patent No.: US 6,360,609 B1
(45) Date of Patent: Mar. 26, 2002

(54) METHOD AND SYSTEM FOR INTERPRETING AND UTILIZING MULTIMODE DISPERSIVE ACOUSTIC GUIDED WAVES

(75) Inventor: Shi-Chang Wooh, Bedford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/736,628

(22) Filed: Dec. 15, 2000

Related U.S. Application Data
(60) Provisional application No. 60/184,260, filed on Feb. 23, 2000.

(51) Int. Cl.$^7$ .......................... G01N 29/06; G01N 29/18
(52) U.S. Cl. ........................................................ 73/602
(58) Field of Search .................. 73/597, 598, 599, 73/600, 602, 620, 624, 628, 627

(56) References Cited

U.S. PATENT DOCUMENTS

| | | | | |
|---|---|---|---|---|
| 4,372,163 A | * | 2/1983 | Tittman et al. ................ | 73/602 |
| 4,688,429 A | * | 8/1987 | Holroyd ...................... | 73/602 |
| 5,035,144 A | * | 7/1991 | Aussel ........................ | 73/602 |
| 5,438,872 A | * | 8/1995 | Kobayashi et al. ........... | 73/597 |
| 5,629,485 A | * | 5/1997 | Rose et al. .................. | 73/599 |
| 5,724,138 A | | 3/1998 | Reich et al. ................. | 356/359 |
| 5,767,410 A | * | 6/1998 | Lareau et al. ................ | 73/623 |
| 5,804,727 A | * | 9/1998 | Lu et al. ..................... | 73/597 |
| 5,814,730 A | | 9/1998 | Brodeur et al. .............. | 73/597 |

FOREIGN PATENT DOCUMENTS
WO    WO 96/12951    5/1996

OTHER PUBLICATIONS

Quantitative Nondestructive Evaluation, by Donald O. Thompson and Dale E. Chiment, Center for NDE and Department of Aerospace Engineering and Engineering Mechanics, Iowa State University, American Institute of Physics, Melville, NY, AIP Conference Proceedings, vol. 19A, pp. 831–838, Jul. 25–30, 1999.

* cited by examiner

Primary Examiner—Hezron Williams
Assistant Examiner—Rose M. Miller
(74) Attorney, Agent, or Firm—Iandiorio & Teska

(57) ABSTRACT

A method and system of locating discontinuities, measuring distances, locating unknown sources, and measuring the thickness of multimode dispersive medium includes sensing a multimode dispersive acoustic guided wave and frequency decomposing that wave using spectral temporal analysis; selecting a frequency which identifies a group delay of the guided wave for each mode occurring at that frequency; selecting a mode from the group delays of the selected mode, determining the group velocity from the dispersion curves and computing the desired parameter.

16 Claims, 12 Drawing Sheets

METHOD AND SYSTEM FOR INTERPRETING AND UTILIZING MULTIMODE DISPERSIVE ACOUSTIC GUIDED WAVES

RELATED APPLICATIONS

This application claims priority of U.S. Provisional application Ser. No. 60/184,260 filed Feb. 23, 2000, entitled METHOD AND APPARATUS FOR DETERMINING IN-PLANE LOCATIONS OF FLAWS IN PLATES.

FIELD OF INVENTION

This invention relates to a method and system for determining the group delay of a multimode, dispersive acoustic guided wave, and more particularly to systems and methods which employ the group delays to determine thickness, locate discontinuities, measure distances, and locate the source in multimode dispersive mediums.

BACKGROUND OF INVENTION

The merits of Lamb wave testing for the nondestructive evaluation (NDE) of thin plates and pipes are well known. When a large area of a structure is to be inspected, Lamb waves are more attractive than bulk waves since they can propagate over long distances to inspect a wider area. However, it is a great misfortune that Lamb waves are multimode by nature. That is, there exist at least two wave modes at any given frequency, thus making the signals complicated and difficult to interpret. Further they are dispersive, meaning that for any given mode the velocity of the waves varies with frequency.

In general, there are two approaches taken to address this unfavorable circumstance. The first coaxes a single mode into dominance. The other accepts the multimode nature of the signal and treats it at a single analysis level.

However, this latter approach has not lent itself to determining distances so that the locations of a flaw or boundary, the location of an unknown acoustic source, or the distance between positions could be determined in a multimode dispersive medium.

SUMMARY OF THE INVENTION

It is therefore an object of this invention to provide an improved method and system for interpreting multimode dispersive signals.

It is a further object of this invention to provide such an improved method and system which uses time-frequency analysis or spectrotemporal analysis to interpret multimode dispersive signals.

It is a further object of this invention to provide such an improved method and system which can determine flaw location, source location, distances and even thickness of multimode dispersive media.

It is a further object of this invention to provided such an improved method and system which calculates group delays in multimode dispersive media.

The invention results from the realization that a simple and effective determination of group delays in multimode dispersive media can be achieved by frequency decomposing multimode dispersive acoustic guided waves and selecting a frequency which identifies the group delays for each mode occurring at that frequency and using that group delays in conjunction with either the group velocities or distance to obtain the other to locate the source of the waves, flaw locations, distances and thickness.

This invention features a method of locating discontinuities in a multimode dispersive medium including exciting at a first position, a multimode dispersive acoustic guided wave in a medium and sensing a second position, both a direct arrival and the reflected multimode dispersive acoustic guided wave. The multimode dispersive acoustic guided wave is frequency decomposed using a spectro-temporal analysis and then a frequency is selected which identifies the group delay, $t_g$, of the direct and reflected guided waves for each mode occurring at that frequency. A mode is selected and a determination is made of the time difference, $\Delta t_g$, between the direct and reflected signals from the group delays of the selected mode. The group velocity $c_g$ is determined from the dispersion curves and the distance L between the discontinuity and the second position is computed according to the expression $L = c_g \cdot \Delta t_g / 2$.

The invention also features a method of distance measurement between positions on a multimode dispersive medium including exciting at a first position a multimode dispersive acoustic guided wave in the medium and sensing at a second position the multimode dispersive acoustic guided wave. The multimode dispersive acoustic guided wave is frequency decomposed using spectral temporal analysis. A frequency is selected which identifies the group delay $t_g$ of the guided wave for each mode occurring at that frequency. A mode is selected and a determination is made of the group delays $t_g$ from the first position. The group velocity $c_g$ is determined from the dispersion curve and the distance L between the two positions is computed from the group delay $t_g$ and group velocity $c_g$.

This invention also relates to a method of locating a source in a multimode dispersive medium including sensing at each of a plurality of positions a different multimode dispersive acoustic guided wave emanating from a source and frequency decomposing each of the multimode dispersive acoustic guided waves using spectrotemporal analysis. A frequency is selected which identifies the group delay $t_g$ of each guided wave for each mode occurring at that frequency. A mode is selected and a determination is made of the group delays $t_{gn}$ of the selected mode for each guided wave. The group velocity $c_{gn}$ is determined from the dispersion curves for each guided wave. The difference between pairs of group delays is calculated and they are multiplied by their respective group velocities to obtain the differences between pairs or distances of the positions from the source. The distance differences are combined to obtain the location of the source.

This invention also features a method of thickness measurement in a multimode dispersive medium including exciting in a first position a multimode dispersive acoustic guided wave in the medium and sensing at a second position the multimode dispersive acoustic guided wave. The multimode dispersive acoustic guided wave is frequency decomposed using spectro-temporal analysis. A frequency is selected which identifies the group delay $t_g$ of the guided wave for each mode occurring at that frequency. A mode is selected and a determination is made of the group delays from the first position. The distance L is identified between the first and the second positions. A mode is selected and a determination is made of the group delay $t_g$ from the first position. The group velocity $c_g$ is calculated in accordance with $c_g$ $$c_g = \frac{L}{t_g}$$

and a determination is made of the thickness from the dispersion relationship.

In a preferred embodiment the sensing occurs at a plurality of second positions surrounding the first position.

This invention also relates to a system for locating discontinuities in a multimode dispersive medium comprising means for exciting at a first position a multimode dispersive acoustic guided wave in a medium and means for sensing at a second position both the direct and reflected multimode dispersive acoustic guided wave. There are means for frequency decomposing the multimode dispersive acoustic guided wave using spectral temporal analysis and means for selecting a frequency which identifies the group delay $t_g$ of the direct and reflective guided wave for each mode occurring at that frequency. There are means for selecting a mode and determining the time difference $\Delta t_g$ between the direct and reflected signals from the group delays of the selected mode. There are means for determining the group velocity $c_g$ from the dispersion curves and means for computing the distance L between the discontinuity and the second position in accordance with the expression $L = c_g \cdot \Delta t_g / 2$.

This invention also features a system for distance measurement between positions on a multimode dispersive medium including means for exciting at a first position a multimode dispersive acoustic guided wave in the medium and means for sensing at a second position the multimode dispersive acoustic guided wave. There are means for frequency decomposing the multimode dispersive acoustic guided wave using spectral temporal analysis and means for selecting a frequency which identifies the group delay $t_g$ of the guided wave for each mode occurring at that frequency. There are means for selecting a mode and determining the group delays $t_g$ from the first position. There are also means for determining the group velocity $c_g$ for the dispersion curves and means for computing the distance L between the two positions from the group delay $t_g$ and group velocity $c_g$ in accordance with the expression $L = t_g \cdot c_g$.

This invention also features a system for locating a source in a multimode dispersive medium including means for sensing each of a plurality of positions a different multimode dispersive acoustic guided wave emanating from a source and means for frequency decomposing each of the multimode dispersive acoustic guided waves using spectral temporal analysis. There are means for selecting a frequency which identifies the group delay $t_g$ of each guided wave for each mode occurring at that frequency and means for selecting a mode in determining the group delays $t_{gn}$ of the selected mode for each guided wave. There are means for determining the group velocity $t_{gn}$ for the dispersion curves for each guided wave and means for calculating the difference between pairs of group delays and multiplying them by their respective group velocity to obtain the differences between pairs of distances of the positions of the source. There are also means for combining the distance differences to obtain the location of the source.

This invention also features to a system for thickness measurement in a multimode dispersive medium including means for exciting in a first position a multimode dispersive acoustic guided wave in the medium and means for sensing in a second position the multimode dispersive acoustic guided wave. There are means for frequency decomposing the multimode dispersive acoustic guided wave using spectral temporal analysis and means for selecting a frequency which identifies the group delay $t_g$ of the guided wave for each mode occurring at that frequency. There are means for selecting a mode and determining the group delays from the first position. There are means for identifying the distance L between the first and second positions, means for selecting a mode and determining the group delay $t_g$ for the first position, and means for calculating the group velocity $c_g$ in accordance with the expression $c_g = L/t_g$, and there are means for determining thickness from the dispersion relationship.

In a preferred embodiment, the means for sensing includes sensor means at a plurality of positions surrounding the first position.

BRIEF DESCRIPTION OF THE DRAWINGS

Other objects, features and advantages will occur to those skilled in the art from the following description of a preferred embodiment and the accompanying drawings, in which.

PREFERRED EMBODIMENT

Figure 1A:
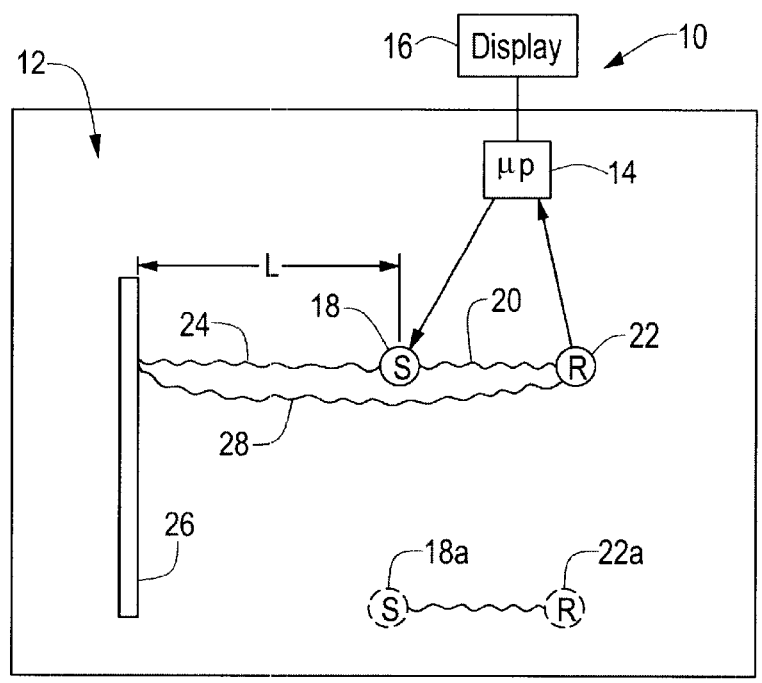
FIG. 1A is a schematic plan view of a system according to this invention for locating a flaw in a multimode dispersive medium.
Figure 1B:
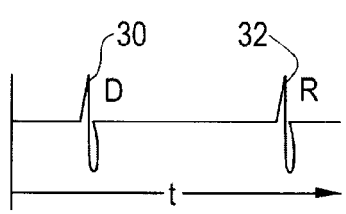
FIG. 1B is a graphical idealized representation of the direct and return signals that occur in the operation of the system of FIG. 1A.
Figure 2:
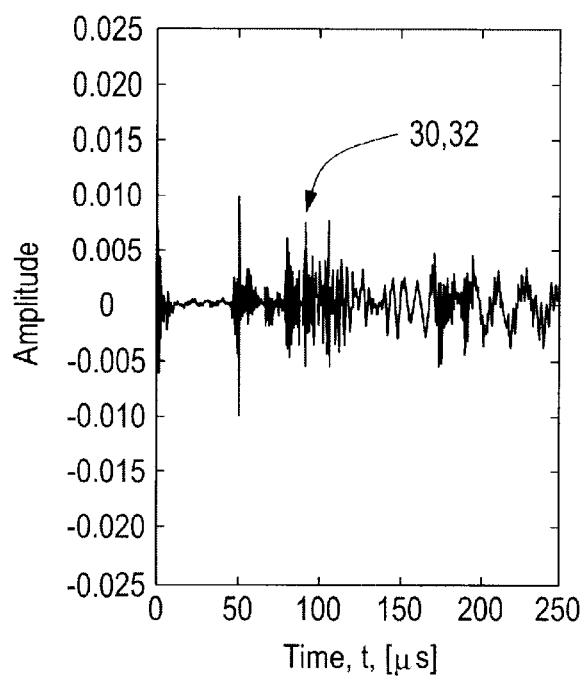
FIG. 2 is a more detailed view of the actual direct and return signals that occur in the operation of the system of FIG. 1A.

There is shown in FIG. 1A a system 10 for locating flaws or discontinuities in a multimode dispersive medium 12. The system includes a microprocessor 14 and a display 16. Microprocessor 14 energizes a source 18 which may be, for example, a laser, a piezoelectric actuator or even a hammer to induce an acoustic guided wave in medium 12. The wave emanates in a first direction 20 to directly strike receiver 22. It also propagates in a second direction 24 where it strikes flaw 26 and returns along path 28 to receiver 22. The receiver could be a laser interferometer, a piezoelectric sensor, an accelerometer, or even a strain gage. The distance L between source 18 and flaw 26 is desired to be known. The distance between the source 18 and receiver 22 is known. In idealized form the direct wave moving along path 20 is shown at 30 in FIG. 1B and the return signal moving along path 24 and 28 is shown at 32. All that is necessary is for the wave velocity and time between the two waves to be determined from which the distance L can easily be calculated. However, unfortunately the real waves are no where near as neat as those shown at 30 and 32. Actually, they appear in combination as shown in FIG. 2 at 30, 32 where both the direct and the return wave are combined in the waveform shown. It is a difficult problem to determine the time between the occurrence of the direct wave and the return wave in the practical situation as shown in FIG. 2. This invention provides a new approach to that problem.

Figure 3:
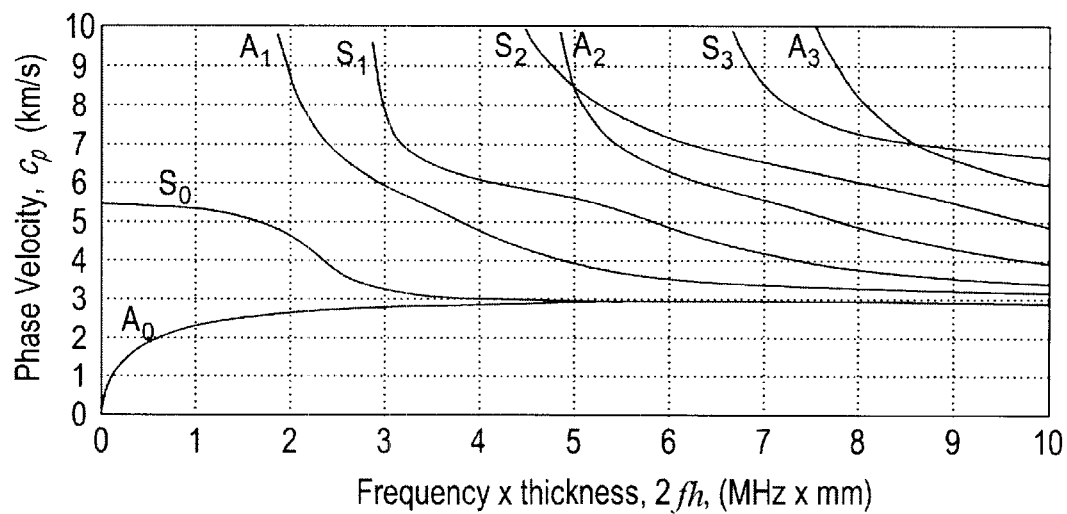
FIGS. 3 and 4 are dispersion curves showing the phase and group velocities, respectively, for a number of modes for an aluminum plate of thickness 2h.
Figure 4:
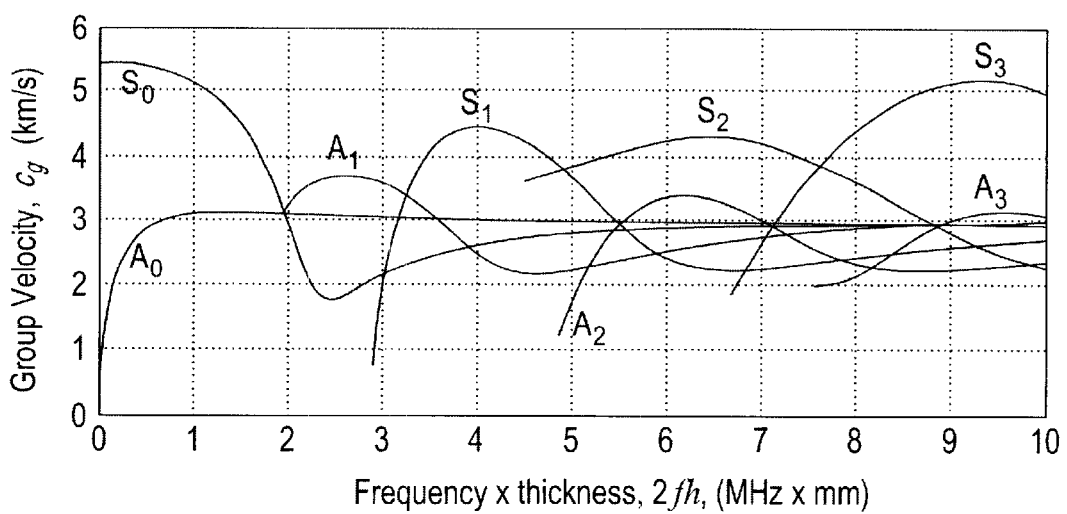

The acoustic guided waves which propagate in medium 12 are multimode. That means each mode has a plurality of modes and each of those modes has a phase velocity which varies with the frequency of the particular mode. These modes $S_0$, $A_0$–$S_3$, $A_3$ are shown in FIG. 3 and are known as the dispersion characteristics. Since the waves are dispersive, that is they travel at different speeds at different frequencies, they beat or interfere to form wave packets which have group velocities in group delays. These group dispersive characteristics are shown in FIG. 4 which exhibits group velocity variation with respect to frequency and thickness for the same modes $S_0$, $A_0$–$S_3$, $A_3$. The group velocity dispersion characteristics in FIG. 4 can be calculated from the phase velocity dispersion characteristics in FIG. 3 as is well known.

Figure 5A:
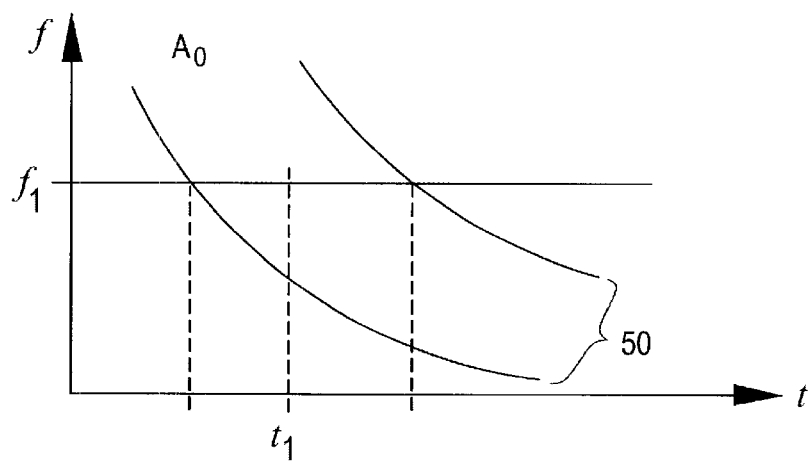
FIG. 5A illustrates the change of frequency with respect to time in a single mode $A_0$.
Figure 6:
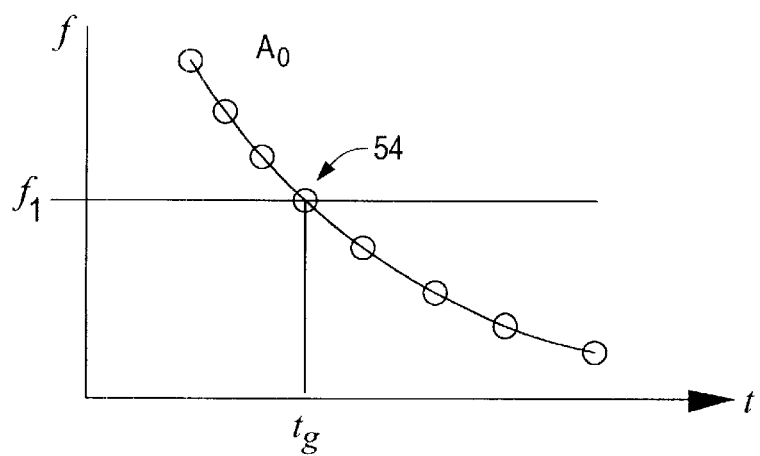
FIG. 6 illustrates a group delay curve formed from the range of frequencies indicated in FIG. 5A employing the maxima determined as shown in FIG. 5B.
Figure 7:
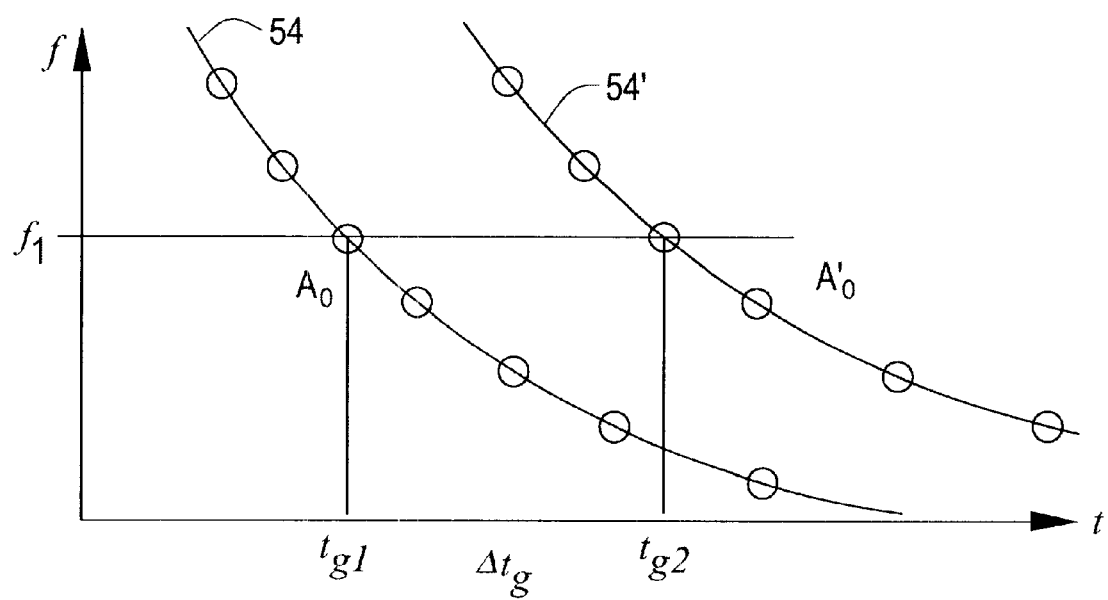
FIG. 7 is a view similar to FIG. 6 showing the group delay curve for the direct wave mode $A_0$ and the return wave mode $A_0'$ resulting from the use of the maxima as shown in FIG. 6.

In accordance with this invention, the guided waves including the direct and the return waves 30 and 32 shown in FIG. 2 are analyzed in the time-frequency domain using a spectrotemporal analysis such as wavelet, short time Fourier transform, Wigner-Ville or empirical decomposition. A further discussion of the time frequency analysis of broadband dispersive waves appears in "Review of Progress and Quantitative Nondestructive Evaluations", vol. 19, Kluwer Academic/Plenum Press, New York, N.Y., *Time-Frequency Analysis of Broadband Dispersive Waves Using the Wavelet Transform*, Shi-Chang Wooh and Karen Veroy, pg. 831–838, Summer 2000. This technique also known as frequency decomposition is shown in FIG. 5A where the frequency response 50 for a particular mode such as $A_0$ is shown as a band of frequencies. This is so because of the wide frequency band characteristic of the single mode. In accordance with this invention, a spectral amplitude variation is identified as a function of time for a fixed frequency $f_1$. The maxima for a number of different frequencies in addition to $f_1$ may be selected from the band of frequencies 50 to construct the spectral temporal characteristic 54, FIG. 6, for a range of the frequencies. Using this characteristic, the arrival time $t_g$ can be determined for the particular frequency for this mode $A_0$. In order to determine the actual distance L, FIG. 1A, characteristics 54 and 54' are constructed as shown in FIG. 7. One for $A_0$ and one for $A_0'$ where $A_0$ represents the direct wave, and $A_0'$ represents the return wave. The intersection of the chosen frequency $f_1$ with the characteristics 54 and 54' give the times $t_{g1}$ and $t_{g2}$. The time delay represented between them is $\Delta t_g$. The length L, FIG. 1 can now be calculated from the formula $$L = \frac{\Delta t_g}{2} \cdot c_g$$

where $c_g$ is the group velocity which can be determined, for example, for the chosen frequency from FIG. 4.

Figure 5B:
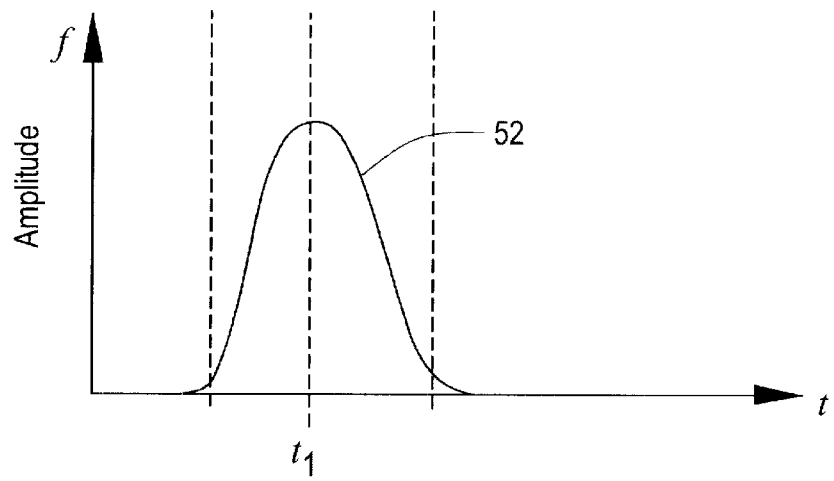
FIG. 5B is an example of the variation with time of the amplitude of a particular frequency selected in FIG. 5A.
Figure 8A:
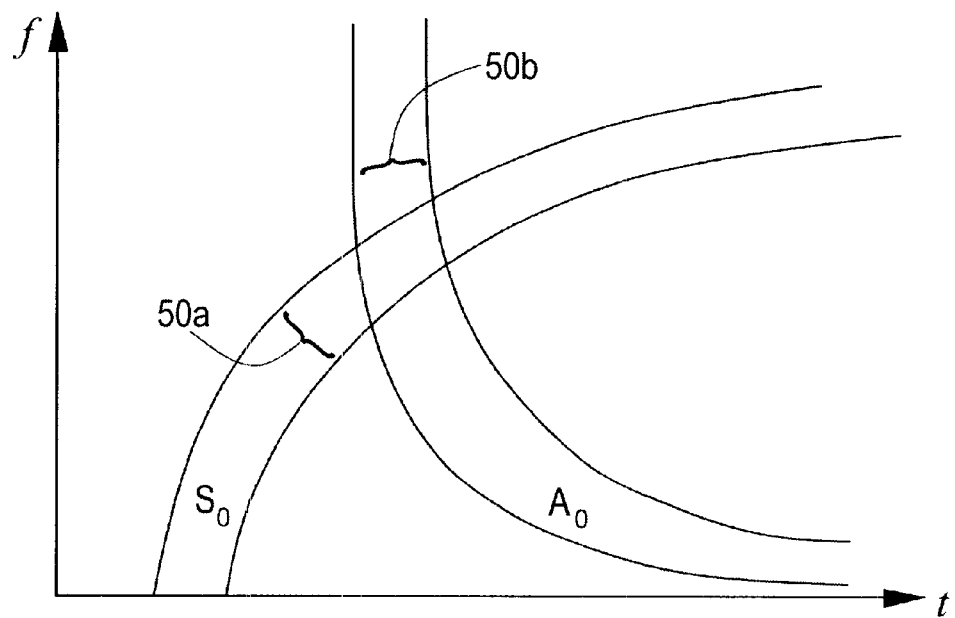
FIG. 8A is a view similar to FIG. 5A showing the band of frequencies for two modes $A_0$ and $S_0$.
Figure 8B:
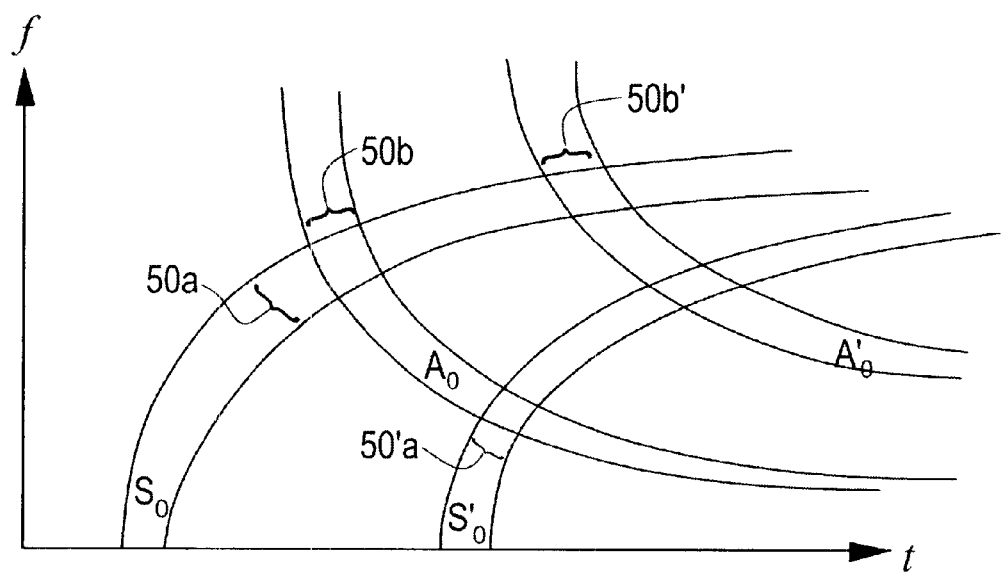
FIG. 8B is a view similar to FIG. 8A, but showing the bands of frequencies for both the direct and the return signals for two modes $A_0$, $S_0$, $A_0'$ and $S_0'$.
Figure 9:
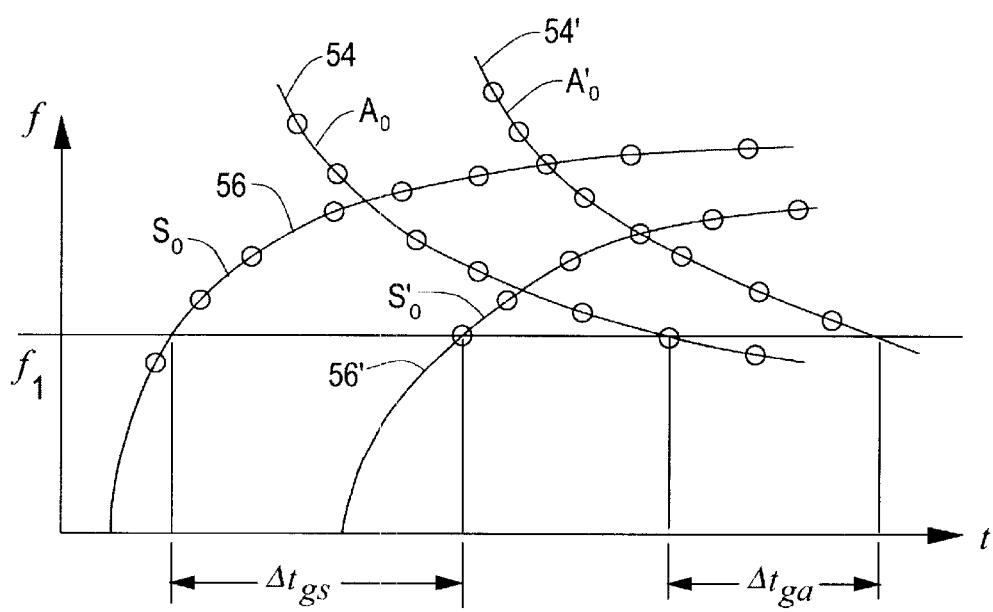
FIG. 9 is a view similar to FIG. 6 of the group delays for modes $A_0$, $A_0'$, $S_0'$ and $S_0'$ showing the group delay time differences $\Delta t_{gA}$, $\Delta t_{gS}$.

Although up to now the discussion of the time frequency analysis or frequency decomposition has been explained with respect to a single mode there are typically more than one mode present. When that is the case, as shown in FIG. 8A there will be two spectrotemporal characteristics 50a and 50b for mode $S_0$ and $A_0$, respectively. When dealing with both the direct and the return waves there are actually four such spectrotemporal characteristics 50a, 50a', 50b, and 50b', FIG. 8B. Although FIGS. 8 and 9 refer only to two modes, this is not a necessary limitation of the invention as any number of modes can be used and any mode can be selected. These characteristic curves and the maxima as explained with respect to FIGS. 5A and 5B can be used to create the spectrotemporal characteristic curves as shown in FIG. 9 in the same way as curve 50 was used to construct curve 54. This results in the two characteristics 54 and 54' representing the direct $A_0$ and return $A_0'$ waves and characteristic curves 56 and 56' representing modes $S_0$ and $S_0'$. This provides two $\Delta t_g$ values as shown in FIG. 9, either one or which can be used to calculate L as previously described. Note that $\Delta t_{gs}$ with respect to $S_0$ mode and $\Delta t_{ga}$ with respect to the $A_0'$ mode have different values. But, these will correspond to different group velocities and so the resulting value computed for L will be the same.

Figure 10:
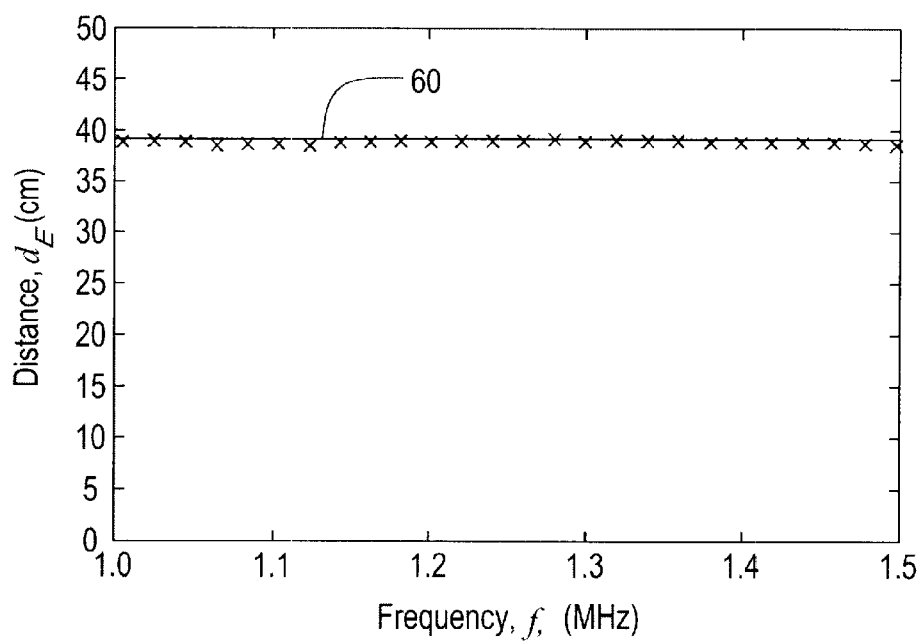
FIG. 10 is a simplified illustration of the constancy of the distance calculatable according to this invention over a range of frequencies.

This is demonstrated in FIG. 10 where having carried out the frequency decomposition or spectro-temporal analysis for a number of frequencies the value of L, FIG. 10, remains virtually constant as shown at 60. According to this invention, the spectrotemporal analysis can be used to perform a number of different functions with respect to multi-mode dispersive media. For example, the location of a flaw may be determined as already discussed, the measurement of a distance between two points on the medium may be found. The location of an unknown source on or in a medium may be determined, and the thickness of the medium may be measured. The implementation of all of the following methods is accomplished in a microprocessor as shown in FIG. 1 which may be a part of a desktop computer.

Figure 11:
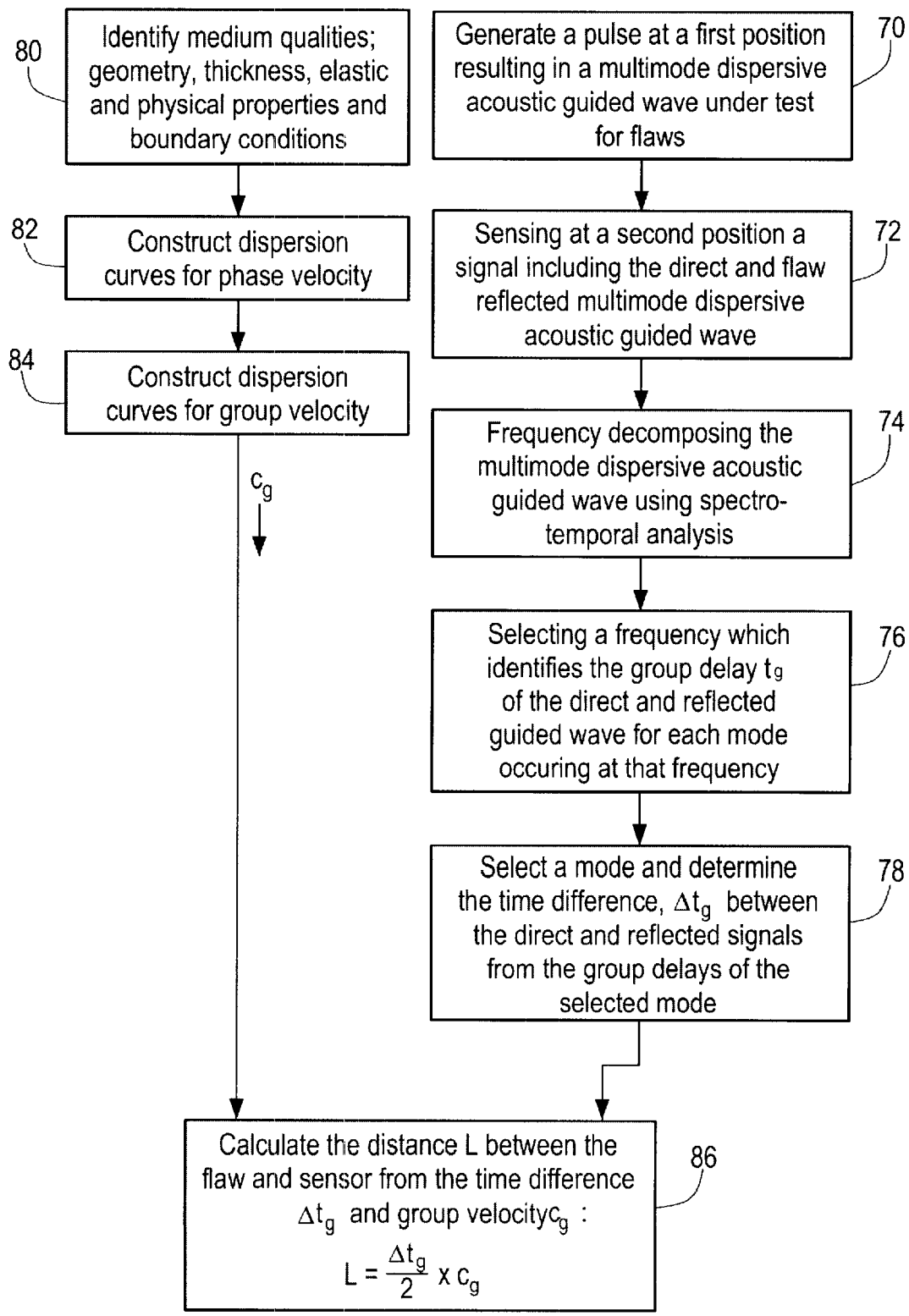
FIG. 11 is a block diagram flow chart showing the computing of flaw location according to this invention.

Flaw location, that is, the calculation of the distance L between the receiver and flaw begins with the generation of the pulse at a first position resulting in a multi-mode dispersive acoustic guided wave in a medium under test for flaws in step 70, FIG. 11. Next, there is sensed at a second position a signal including the direct and flaw-reflected multimode dispersive acoustic guided wave in step 72. In step 74, the multimode dispersive guided wave is frequency-decomposed using a spectro-temporal analysis. In step 76, a frequency is selected which identifies the group delay $t_g$ of the direct and reflected guided wave for each mode occurring at that frequency. A mode is then selected in step 78 and a determination is made of the time difference $\Delta t_g$ between the direct and reflected signals from the group delays of the reflected mode. In parallel with this, the medium qualities are identified in step 80: that is, its geometry, thickness, the elastic and physical properties, and boundary conditions. The dispersion data or curves for phase velocity such as shown in FIG. 3 are constructed in step 82 and those for the group velocity as shown in FIG. 4 are constructed in step 84.

The group velocity $c_g$ is provided in step 86 to calculate the distance L between the flaw and the sensor from the time $\Delta t_g$ and the group velocity $c_g$ using the equation $$L = \frac{\Delta t_g}{2} \cdot c_g.$$

Figure 12:
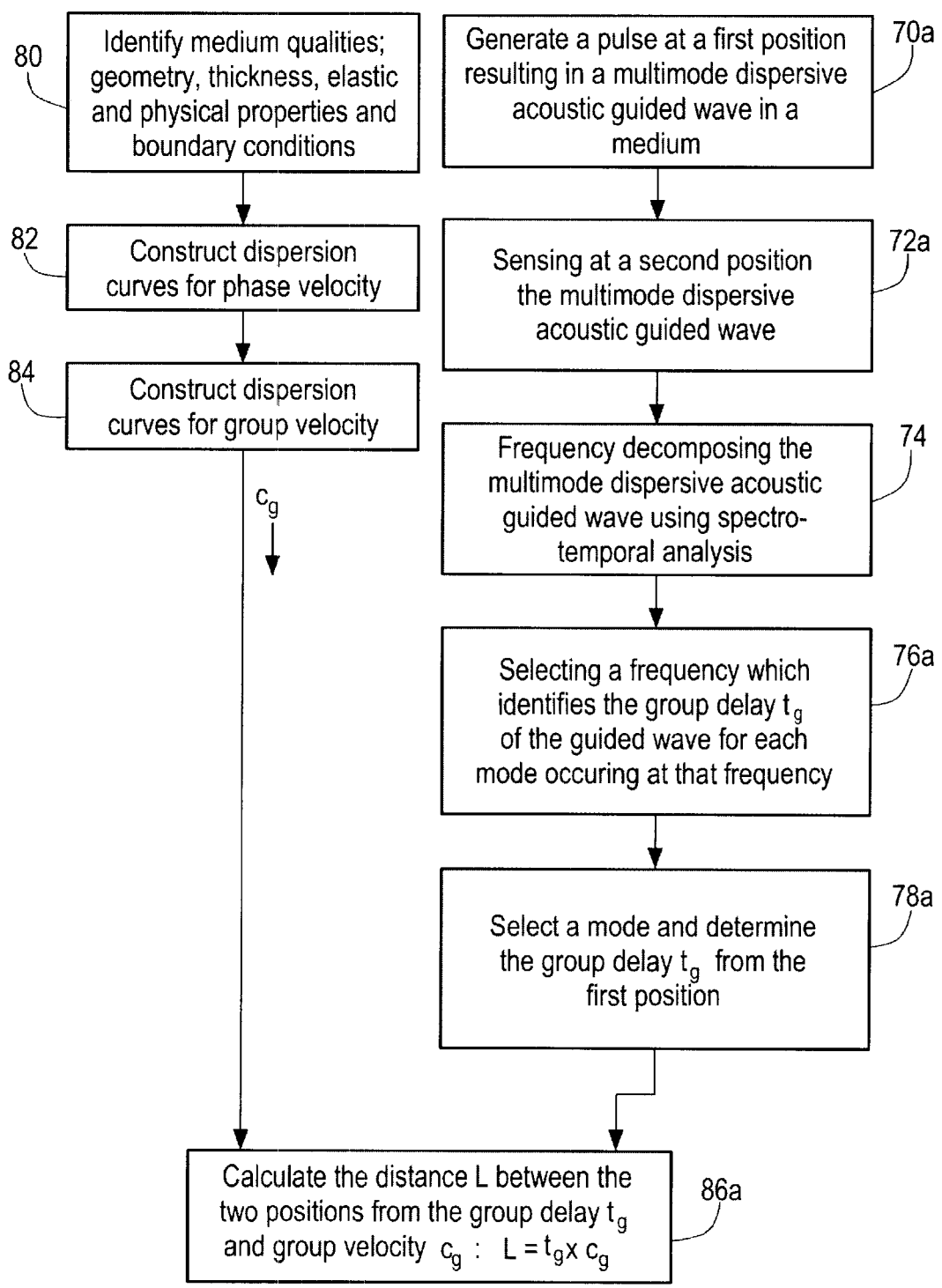
FIG. 12 is a view similar to FIG. 11 showing a computing of the distance measurement according to this invention.

The distance measurement such as between source 18a and receiver 22a in FIG. 1 can be made in accordance with FIG. 12 where like steps have been given like numbers, and similar steps, like numbers accompanied by an A. The distance measurement calculated in according to the expression $L=t_g \cdot c_g$. A pulse is generated at a first position, resulting in a multimode dispersive acoustic guided wave in a medium in step 70a. Then at a second position, there is sensed the multimode acoustic guided wave in step 72a. Frequency decomposition occurs in step 74 the same as in FIG. 11. Then in step 76a, a frequency is selected which identifies the group delay $t_g$ of the guided wave for each mode occurring at that frequency. In step 78a, a mode is selected and the group delay $t_g$ is determined from the first position. The first position being the source, the second position being the receiver. Following the execution of steps 82 and 84 as previously explained with respect to FIG. 11, the value for the group velocity $c_g$ is used in step 86a to calculate the distance L between the two positions from the group delay $t_g$ and velocity $c_g$. Namely, $L=t_g \cdot c_g$.

Figure 13:
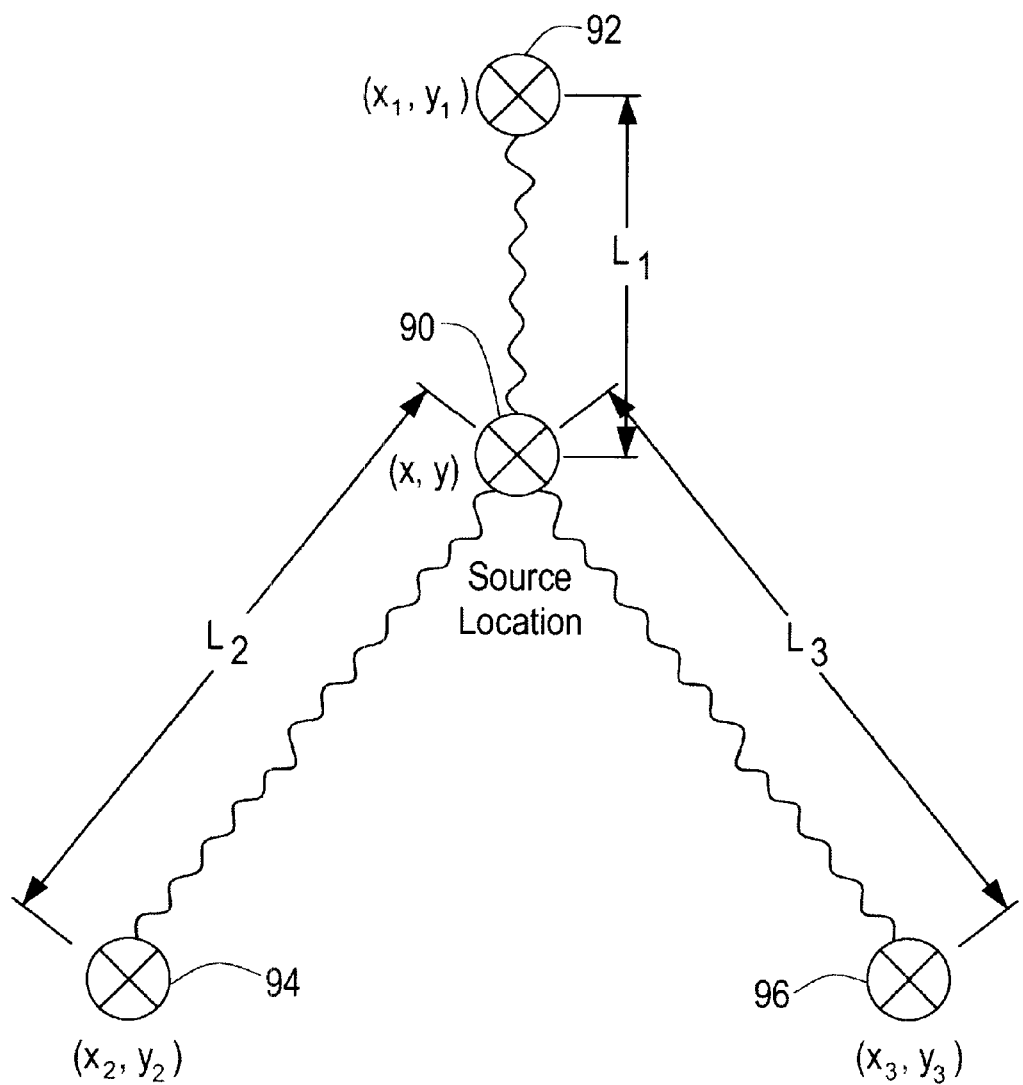
FIG. 13 is a diagrammatic view showing an arrangement of sensors used to identify the location of an unknown source of multimode dispersive acoustic guided waves.
Figure 14:
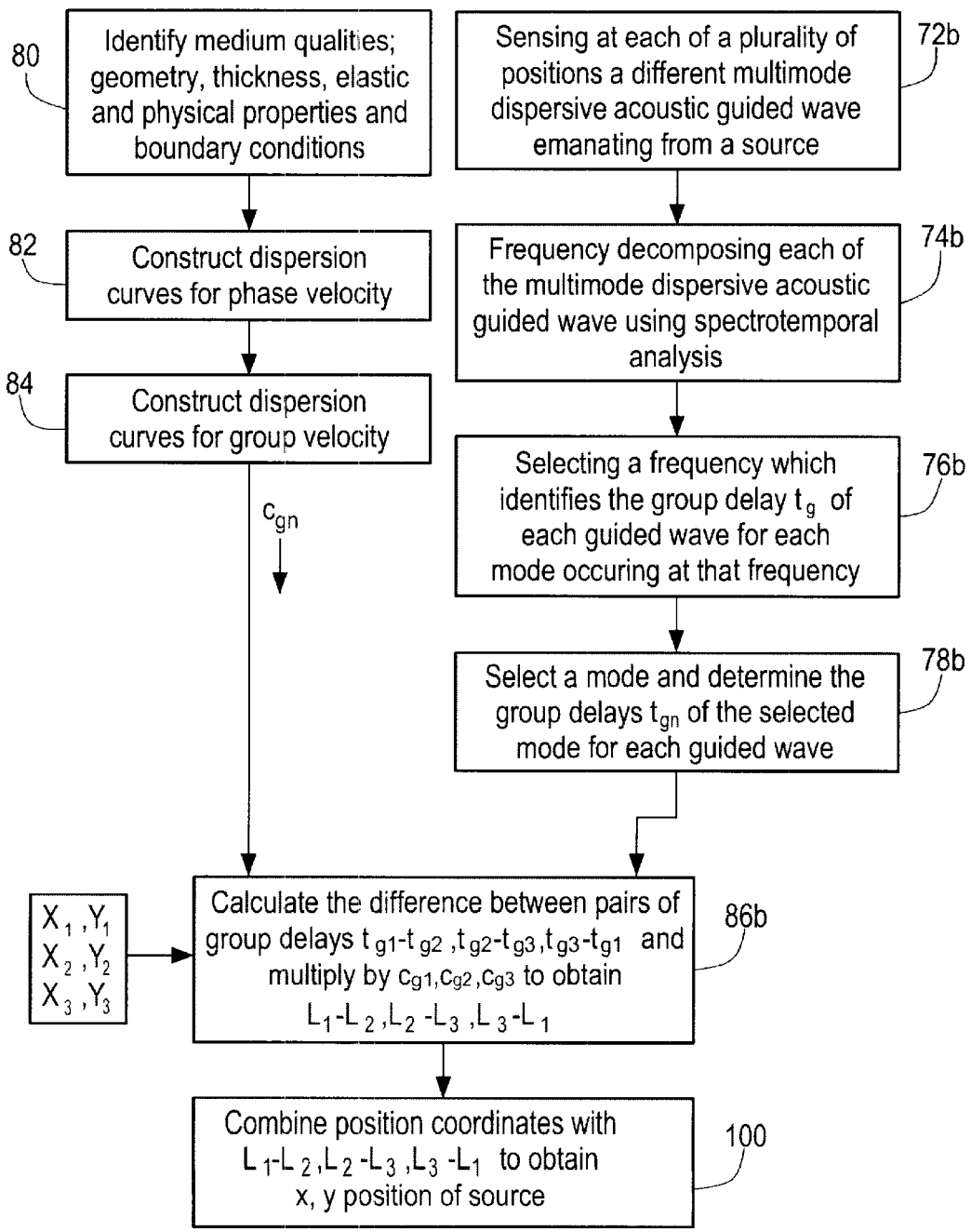
FIG. 14 is a flow chart similar to those shown in FIGS. 11 and 12 showing the computation of the position of an unknown source in accordance with this invention.

Being able to determine the distance in this manner enables a further application of the invention as shown in FIG. 13 where, for example, a source 90, FIG. 13 at an unknown location x,y can actually by located using three sensors 92, 94, and 96 located at $x_1$, $y_1$; $x_2$, $Y_2$; $x_3$, $y_3$, respectively. First the distances $L_1$, $L_2$, and $L_3$ are calculated, then they are combined by triangulation to obtain x,y as explained in FIG. 14 where like parts have been given like numbers and similar parts like numbers accompanied by a lower case b. In step 72b, there is sensed in each of a plurality of positions, a different multimode dispersion acoustic guided wave emanating from the source. There is then a frequency decomposition of each of the multimode dispersive acoustic guided waves using spectro-temporal analysis. Following this in step 76b, a frequency is selected which identifies the group delay $t_g$ of each guided wave for each mode occurring at that frequency. Then in step 78b, a mode is selected and a determination is made of the group delays $t_g$ of the selected mode for each guided wave. The group delay $t_{gn}$, the velocities $c_{gn}$, and the position of each receiver $x_1$, $y_1$, $x_2$, $Y_2$, and $X_3$, $y_3$, are combined in step 86b to first calculate the difference between the pairs of group delays $t_{g1}-t_{g2}$, $t_{g2}-t_{g3}$, and $t_{g3}-t_{g1}$, and multiply them by their respective group velocity $c_{g1}$, $C_{g2}$, $C_{g3}$, to obtain $L_1-L_2$, $L_2-L_3$, $L_3-L_1$. Finally, in step 100, these positions are combined to obtain the x,y position of the source. One application for locating a source is to detect and locate the position of an unknown failure which has been detected by the system.

Figure 15:
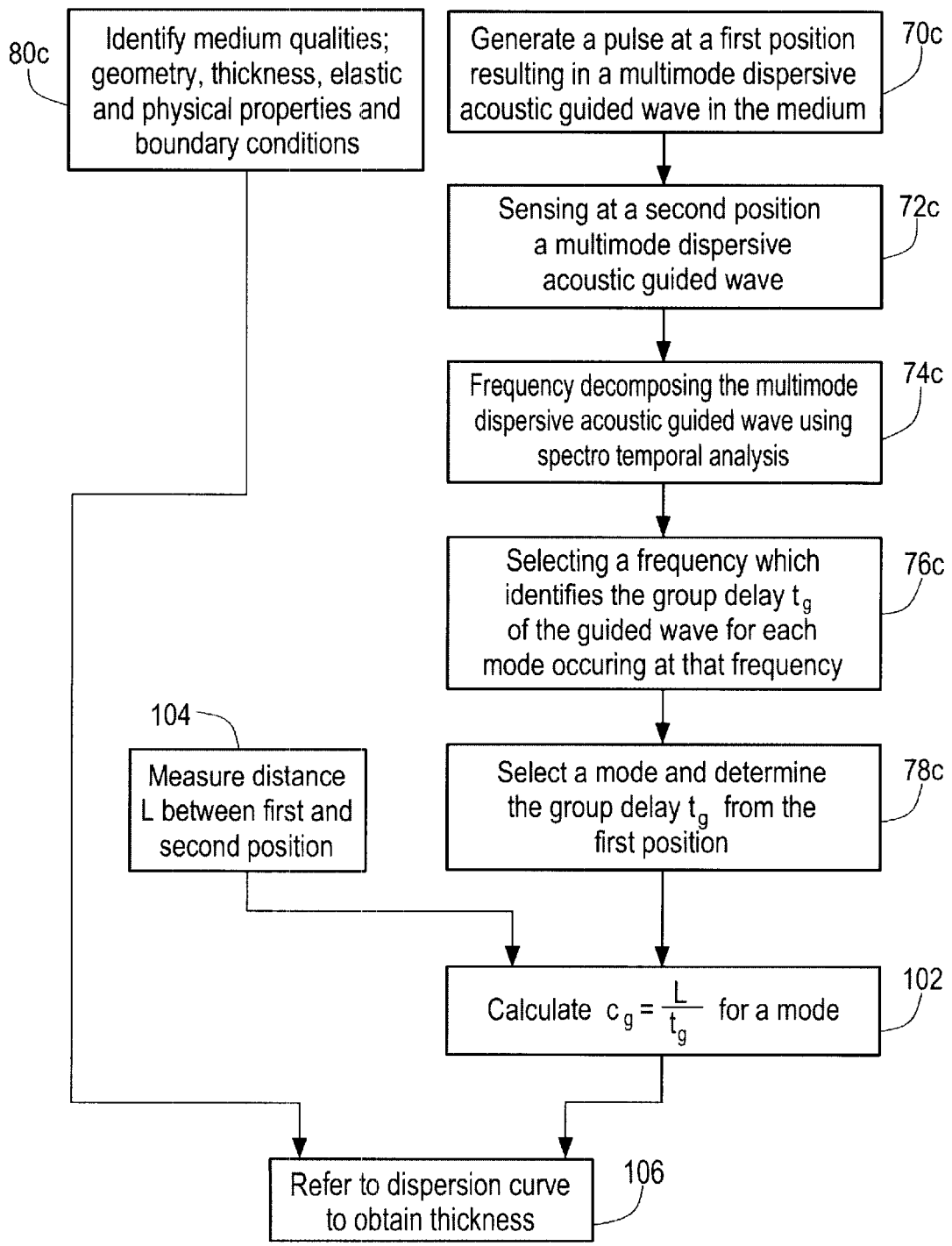
FIG. 15 is a flow chart similar to FIGS. 11, 12 and 14 showing the calculation of the measurement of the thickness of a multimode dispersive medium.

The thickness of the multimode dispersive medium can also be determined in accordance with this invention as shown in FIG. 15. The medium qualities are identified in step 80c. These qualities include geometry, elastic and physical properties and boundary conditions but not thickness in this case, since thickness is going to be determined. In step 70c, a pulse is generated at a first position resulting in a multimode dispersive acoustic guided wave in the medium. In step 72c, there is sensed at a second position a multimode dispersive acoustic guided wave. Then frequency decomposition is done of the multimode dispersive acoustic guided wave using spectro-temporal analysis in step 74c. In step 76c, the frequency is selected which identifies the group delay $t_g$ of the guided wave for each mode occurring at that frequency. In step 78c, a mode is selected and the group delay $t_g$ is selected from the first position. Knowing the time delay $t_g$ from the first position and knowing the distance L between the first and second positions from step 100, the group velocity $c_g$ can be calculated in step 102 using the expression $c_g$ $$c_g = \frac{L}{t_g}$$

calculated $c_g$ and knowing the properties of the medium from step 80c, the system now refers to the dispersion curves, for example, as shown in FIGS. 3 and 4 to obtain the thickness.

Figure 16:
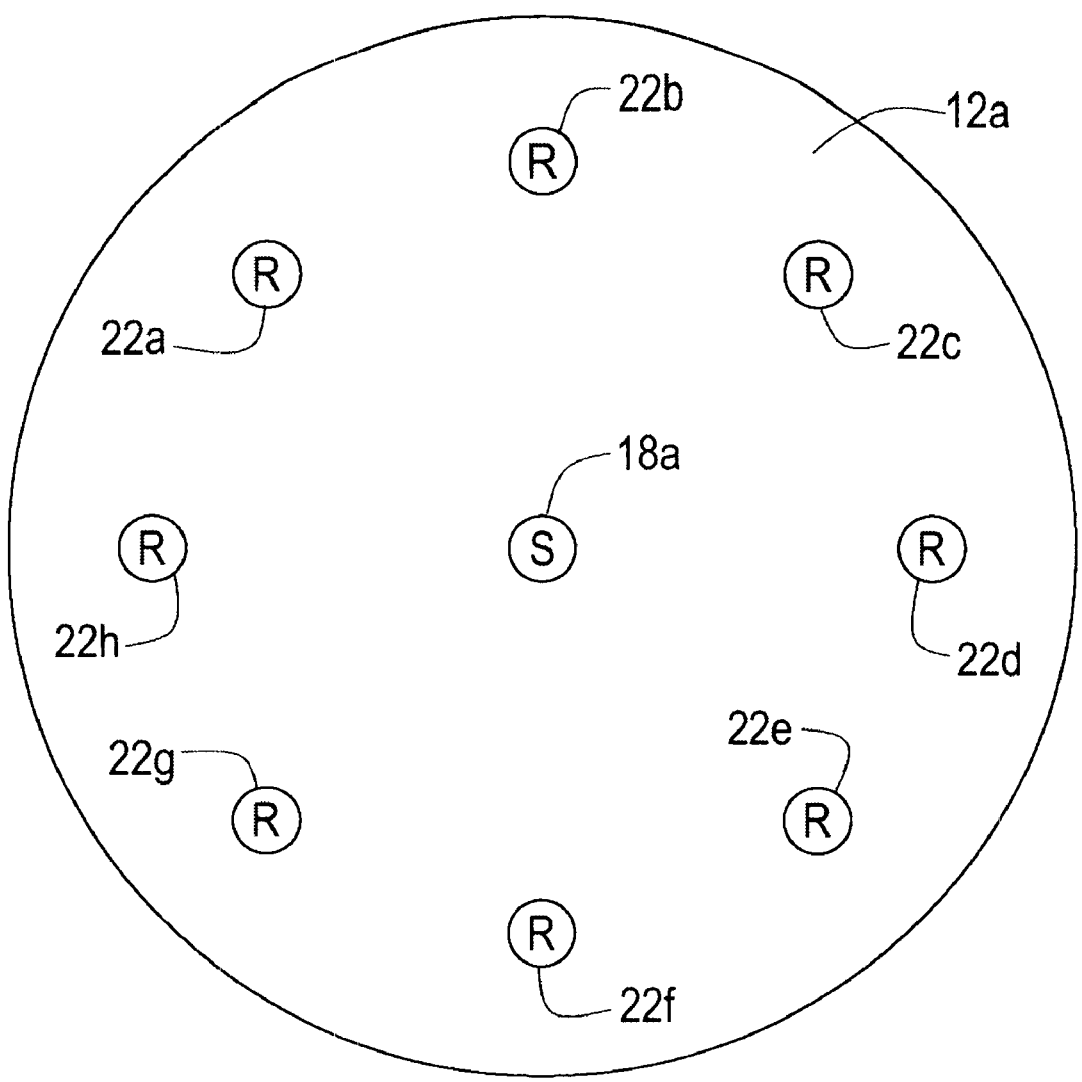
FIG. 16 is a schematic plan view of an arrangement of a source amidst a number of receivers on a multimode dispersive acoustic guided wave medium.

Although thus far, the arrangement of the source and receiver has been simply shown, their relative positions is not a limitation of this invention. For example, as shown in FIG. 1A, the source 18 is between the receiver 22 and flaw 26 but the converse could be true, receiver 22 could be between source 18 and flaw 26. Further as shown in FIG. 16 the source 18a may be placed on a medium 12a with a plurality of receivers 22a–h surrounding it. In this way a wide area can be scanned using a single source by interrogating each of the receivers when source 18a emits a guided wave. Although in this disclosure the medium is generally shown as planar in form, this is not a necessary limitation of the invention. This invention may be used with a number of thin-walled structures including plates, pipe, girders, and the like.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims:

What is claimed is:

1. A method of locating discontinuities in a multimode, dispersive medium comprising:
    exciting at a first position a multimode, dispersive acoustic guided wave in a medium;
    sensing at a second position both the direct arrival and the reflected multimode dispersive acoustic guided wave;
    frequency decomposing the multimode dispersive acoustic guided wave using spectrotemporal analysis;
    selecting a frequency which identifies the group delay, $t_g$, of the direct and reflected guided wave for each mode occurring at that frequency;
    selecting a mode and determining the time difference, $\Delta t_g$, between the direct and reflected signals from the group delays of the selected mode;
    determining the group velocity, $c_g$, from the dispersion curves; and
    computing the distance, L, between the discontinuity and the second position $L=\Delta t_g \cdot c_g/2$.

2. The method of claim 1 further including sensing at a plurality of second positions surrounding the first position.

3. A method of distance measurement between positions on a multimode, dispersive medium comprising:

exciting at a first position a multimode, dispersive acoustic guided wave in the medium;

sensing at a second position the multimode dispersive acoustic guided wave;

frequency decomposing the multimode dispersive acoustic guided wave using spectrotemporal analysis;

selecting a frequency which identified the group delay, $t_g$, of the guided wave for each mode occurring at that frequency;

selecting a mode and determining the group delays, $t_g$, from the first position;

determining the group velocity, $c_g$, from the dispersion curves; and computing the distance, L, between the two positions from the group delay, $t_g$, and group velocity, $c_g$, $L=t_g \cdot c_g$.

4. The method of claim 3 further including sensing at a plurality of second positions surrounding the first position.

5. A method of locating a source in a multimode, dispersive medium comprising:

sensing at each of a plurality of positions different multimode dispersive acoustic guided waves emanating from a source;

frequency decomposing each of the multimode dispersive acoustic guided wave using spectrotemporal analysis;

selecting a frequency which identifies the group delay, $t_g$, of each guided wave for each mode occurring at that frequency;

selecting a mode and determining the group delays, $t_{gn}$, of the selected mode for each guided wave;

determining the group velocity, $t_{gn}$, from the dispersion curves for each guided wave;

calculating the difference between pairs of group delays and multiplying by their respective group velocities to obtain the difference between pairs of distances of the positions from the source; and combining the distance differences to obtain the location of the source.

6. The method of claim 5 further including sensing at a plurality of second positions surrounding the first position.

7. A method of thickness measurement in a multimode, dispersive medium comprising:

exciting at first position a multimode, dispersive acoustic guided wave in the medium;

sensing at a second position the multimode dispersive acoustic guided wave;

frequency decomposing the multimode dispersive acoustic guided wave using spectrotemporal analysis;

selecting a frequency which identifies the group delay, $t_g$, of the guided wave for each mode occurring at that frequency;

selecting a mode and determining the group delays from the first position;

identifying the distance, L, between the first and second positions;

selecting a mode and determining the group delay, $t_g$, from the first position;

calculating the group velocity $$c_g = \frac{L}{t_g};$$

and determining the thickness from the dispersion relationship.

8. The method of claim 7 further including sensing at a plurality of second positions surrounding the first position.

9. A system for locating discontinuities in a multimode, dispersive medium comprising:

means for exciting at a first position a multimode, dispersive acoustic guided wave in a medium;

means for sensing at a second position both the direct arrival and the reflected multimode dispersive acoustic guided wave;

means for frequency decomposing the multimode dispersive acoustic guided wave using spectrotemporal analysis;

means for selecting a frequency which identifies the group delay, $t_g$, of the direct and reflected guided wave for each mode occurring at that frequency;

means for selecting a mode and determining the time difference, $\Delta t_g$, between the direct and reflected signals from the group delays of the selected mode;

means for determining the group velocity, $c_g$, from the dispersion curves; and means for computing the distance, L, between the discontinuity and the second position $L=c_g \cdot \Delta t_g/2$.

10. The system of claim 9 in which said means for sensing includes sensor means at a plurality of second positions surrounding said first position.

11. A system for distance measurement between positions on a multimode, dispersive medium comprising:

means for exciting at first position a multimode, dispersive acoustic guided wave in a medium;

means for sensing at a second position the reflected multimode dispersive acoustic guided wave;

means for frequency decomposing the multimode dispersive acoustic guided wave using spectrotemporal analysis;

means for selecting a frequency which identifies the group delay, $t_g$, of the guided wave for each mode occurring at that frequency;

means for selecting a mode and determining the group delays, $t_g$, from the first position;

means for determining the group velocity, $c_g$, from the dispersion curves; and means for computing the distance, $L=t_g \cdot c_g$, between the two positions from the group delay, $t_g$, and group velocity, $c_g$.

12. The system of claim 11 in which said means for sensing includes sensor means at a plurality of second positions surrounding said first position.

13. A system for locating sources in a multimode, dispersive medium comprising:

means for sensing at each of a plurality of positions a different multimode dispersive acoustic guided wave;

means for frequency decomposing each of the multimode dispersive acoustic guided waves using spectrotemporal analysis;

means for selecting a frequency which identifies the group delay, $t_g$, of each guided wave for each mode occurring at that frequency;

means for selecting a mode and determining the group delays, $t_{gn}$, of the selected mode for each guided wave;

means for determining the group velocity, $c_{gn}$, from the dispersion curves for each guided wave;

means for calculating the difference between pairs of group delays and multiplying by their respective group velocities to obtain the difference between pairs of distances of the positions from the source; and means for combining the distance differences to obtain the location of the source.

14. The method of claim 13 further including sensing at a plurality of second positions surrounding the first position.

15. A system for thickness measurement in a multimode, dispersive medium comprising:

means for exciting at a first position a multimode, dispersive acoustic guided wave in the medium;

means for sensing at a second position the multimode dispersive acoustic guided wave;

means for frequency decomposing the multimode dispersive acoustic guided wave using spectrotemporal analysis;

means for selecting a frequency which identifies the group delay, $t_g$, of the guided wave for each mode occurring at that frequency;

means for selecting a mode and determining the group delays from the first position;

means for identifying the distance, L, between the first and second positions;

means for selecting a mode and determining the group delay, $t_g$, from the first position;

means for calculating the group velocity $$c_g = \frac{L}{t_g};$$

and means for determining the thickness from the dispersion relationship.

16. The method of claim 15 further including sensing at a plurality of second positions surrounding the first position.

* * * * *